(12) United States Patent
Bogenschuetz et al.

(10) Patent No.: US 10,596,015 B2
(45) Date of Patent: *Mar. 24, 2020

(54) INTRALUMINAL VASCULAR PROSTHESIS

(71) Applicant: JOTEC GmbH, Hechingen (DE)

(72) Inventors: Thomas Bogenschuetz, Hechingen-Stein (DE); Franz-Peter Barthold, Balingen (DE)

(73) Assignee: JOTEC GmbH, Hechingen (DE)

(*) Notice: Subject to any disclaimer, the term of this patent is extended or adjusted under 35 U.S.C. 154(b) by 247 days.

This patent is subject to a terminal disclaimer.

(21) Appl. No.: 15/804,660

(22) Filed: Nov. 6, 2017

(65) Prior Publication Data

US 2018/0055664 A1 Mar. 1, 2018

Related U.S. Application Data

(63) Continuation of application No. 14/445,833, filed on Jul. 29, 2014, now Pat. No. 9,833,341, which is a
(Continued)

(30) Foreign Application Priority Data

Feb. 1, 2012 (DE) .......................... 10 2012 100 839

(51) Int. Cl.
*A61F 2/82* (2013.01)
*A61F 2/07* (2013.01)
(Continued)

(52) U.S. Cl.
CPC .................. *A61F 2/82* (2013.01); *A61F 2/07* (2013.01); *A61F 2/89* (2013.01); *A61F 2/90* (2013.01);
(Continued)

(58) Field of Classification Search
CPC ........ A61F 2/07; A61F 2002/075; A61F 2/89; A61F 2002/061; A61F 2002/828; A61F 2/82; A61F 2/90; A61F 2/91; A61F 2/915
See application file for complete search history.

(56) References Cited

U.S. PATENT DOCUMENTS

| 6,152,956 A | 11/2000 | Pierce |
| 2003/0220683 A1 | 11/2003 | Minasian |
(Continued)

FOREIGN PATENT DOCUMENTS

| DE | 695 31 239 | 4/2004 |
| DE | 698 32 218 | 8/2006 |
(Continued)

OTHER PUBLICATIONS

Mailed Aug. 14, 2014—English Translation of the International Preliminary Report on Patentability (Chapter I).
(Continued)

*Primary Examiner* — Katherine M Shi
(74) *Attorney, Agent, or Firm* — Casimir Jones, SC; Robert A. Goetz

(57) ABSTRACT

The invention relates to an intraluminal vascular prosthesis, preferably for implanting in the aortic arch. The prosthesis has a hollow cylindrical body with a first end and a second end; a first vascular prosthesis portion; a second vascular prosthesis portion; and a stent portion which is provided between the first and the second vascular prosthesis portion and which is rigidly connected to said vascular prosthesis portions, said stent portion being free of prosthesis material.

9 Claims, 3 Drawing Sheets

Related U.S. Application Data continuation of application No. PCT/EP2013/052037, filed on Feb. 1, 2013.

(51) Int. Cl.
    *A61F 2/91*     (2013.01)
    *A61F 2/915*     (2013.01)
    *A61F 2/89*     (2013.01)
    *A61F 2/90*     (2013.01)

(52) U.S. Cl.
    CPC ........... *A61F 2/91* (2013.01); *A61F 2002/072* (2013.01); *A61F 2002/9155* (2013.01)

(56) References Cited

U.S. PATENT DOCUMENTS

| | | |
|---|---|---|
| 2004/0106981 A1 | 6/2004 | Zarbatany |
| 2005/0177222 A1 | 8/2005 | Mead |
| 2006/0276883 A1 | 7/2006 | Greenberg et al. |
| 2007/0067014 A1 | 3/2007 | Ke et al. |
| 2007/0112411 A1 | 5/2007 | Obermiller et al. |
| 2008/0132993 A1* | 6/2008 | Rasmussen ............... A61F 2/06 623/1.13 |
| 2010/0094409 A1 | 4/2010 | Barker |
| 2010/0268318 A1 | 10/2010 | Glynn |

FOREIGN PATENT DOCUMENTS

| | | |
|---|---|---|
| EP | 0754016 | 1/1997 |
| EP | 0855170 | 7/1998 |
| JP | 2009-506842 | 2/2009 |
| WO | 95/26695 | 10/1995 |
| WO | 05/058202 | 6/2005 |
| WO | 2007/028086 | 3/2007 |
| WO | 08/130572 | 10/2008 |

OTHER PUBLICATIONS

Examination Report (and English translation) dated Sep. 1, 2015 from related JP Patent Application No. 2014-555223.

* cited by examiner

INTRALUMINAL VASCULAR PROSTHESIS

CROSS REFERENCES TO RELATED APPLICATIONS

This application is a continuation of U.S. patent application Ser. No. 14/445,833, filed Jul. 29, 2014, which is a continuation of international patent application PCT/EP2013/052037, filed on Feb. 1, 2013 designating the U.S., which international patent application has been published in German language and claims priority from German patent application DE 10 2012 100 839.6, filed on Feb. 1, 2012. The entire contents of these priority applications are incorporated herein by reference.

BACKGROUND OF THE INVENTION

The present invention relates to an intraluminal vascular prosthesis, in particular for implanting in the aortic arch, having a hollow cylindrical body with a first end and a second end, wherein the vascular prosthesis has, at its first end, a first vascular prosthesis portion, with successive rings of meandering supports, and a prosthesis material secured on the rings and connecting them.

In particular, the present invention relates to vascular prostheses that are implanted in the area of the aortic arch.

It is generally known for intraluminal vascular prostheses, also referred to as endovascular stents or stent grafts, to be implanted in arteries in order to treat aneurysms. An aneurysm is understood as a widening or bulging of an arterial blood vessel as a consequence of congenital or acquired lesions of the vessel wall. The bulge can affect the vessel wall as a whole or, in what is called a false aneurysm or dissection, blood flows from the lumen of the vessel in between the layers of the vessel wall and tears these apart from one another. Non-treatment of an aneurysm may lead to a rupture of the artery in advanced stages, after which the patient suffers internal bleeding.

Aneurysms often occur in the area of the abdominal aorta (aorta abdominalis) or thoracic aorta (aorta thoracica). For treatment of aneurysms in the abdominal or thoracic aorta, it is already known to stabilize the artery by implantation of a stent, so that a rupture of the vessel is avoided.

The vascular prostheses or implants used for the treatment of such aneurysms generally consist of a hollow cylindrical metal framework of which the jacket surface is covered by a textile or polymer film, i.e. a prosthesis material, such that a hollow cylindrical body is obtained. For implantation, the vascular prosthesis is radially compressed, such that its cross-sectional area is greatly reduced. With the aid of an insertion system, the vascular prosthesis is then brought into the area of the aneurysm, where it is released and, if appropriate, sutured. By virtue of the resilience of the metal frame, the vascular prosthesis expands again to its original shape and in so doing stretches its jacket surface, which lodges inside the blood vessel proximally and distally in relation to the aneurysm. In this way, the blood now flows through the vascular prosthesis, and further loading of an aneurysm is avoided. The metal framework of the vascular prosthesis, covered by the prosthesis material, is composed, for example, of so-called stent rings, which are arranged in succession and are made of a self-expanding material.

An aneurysm can occur not only in the abdominal aorta or thoracic aorta, but also in the ascending branch of the aorta (aorta *ascendens*). The ascending branch of the aorta is connected directly to the heart. Starting from the aortic root (sinus aortae), the ascending branch extends upward in a slightly curved shape away from the heart and merges there into the aortic arch (arcus aortae). The vessels of the head, among others the left and right carotid arteries, branch off in the area of the aortic arch. The aortic arch follows a curve of approximately 180° with a very narrow radius and connects the ascending branch of the aorta to the thoracic aorta and eventually to the abdominal aorta.

An aneurysm or a dissection in the ascending branch of the aorta has hitherto been treated by invasive open surgery. Such surgery has generally required two major interventions to be performed at different times and entails a very extensive, complex and therefore dangerous operation, since it is not just the heart but also the brain and the abdominal organs of the patient that have to be subjected to hypothermic perfusion, i.e. artificial, cold extracorporeal blood flow. However, only a small number of heart surgeons at specialist centers are sufficiently familiar with such a procedure.

In the prior art, no vascular prosthesis, stent system or stent graft system is yet known with which the surgery outlined above could be made easier and performed in a shorter time, and, consequently, there is still a great need for such a system.

An object of the present invention is therefore to make available a system with which the area of the ascending aorta, of the aortic arch and of the descending aorta can be treated quickly and in an uncomplicated manner, and which also allows the procedures outlined above to be performed by less experienced surgeons.

SUMMARY OF THE INVENTION

This and other objects are achieved by an intraluminal vascular prosthesis having a hollow cylindrical body with a first end and a second end, wherein the vascular prosthesis comprises, at its first end, a first vascular prosthesis portion, with successive rings of meandering supports, and a prosthesis material secured on the rings and connecting them, and wherein the vascular prosthesis has, at its second end, a second vascular prosthesis portion which has only a prosthesis material and has no successive rings of meandering supports connected to the prosthesis material, wherein the vascular prosthesis moreover has a stent portion which is provided between the first vascular prosthesis portion and the second vascular prosthesis portion and which is rigidly connected to said vascular prosthesis portions, said stent portion being free of prosthesis material.

By means of the inventive combination of two relatively short vascular prosthesis portions, i.e. a first one constituting a vascular prosthesis portion covered with prosthesis material and a second one composed only of prosthesis material, with a free and uncovered stent portion lying between these vascular prosthesis portions, it is possible to treat the three portions of the aorta, namely the ascending aorta, the aortic arch and the descending aorta, simultaneously and thus significantly reduce the time needed for the surgical intervention. It is thus possible to dispense with resection of the aortic arch, and with all the associated complex perfusion requirements for the brain and lower body, and the intervention can be carried out simply by separating the uppermost portion of the ascending aorta in a short (ca. 10-20 minute) selective head perfusion phase or hypothermic arrest phase in order to insert and release the new vascular prosthesis. It can be inserted and released simply with monitoring by the naked eye or by angioscope.

According to the invention, therefore, an intraluminal vascular prosthesis is for the first time made available with which it is possible to simplify surgical interventions on the aortic arch, or in the ascending aorta, aortic arch and descending aorta, and to greatly reduce the time needed for these interventions. Advantageously, therefore, it is not just highly specialized heart surgeons who can perform the above-described interventions on the aortic arch. Moreover, the vascular prosthesis according to the invention can also be used on severely diseased patients, and also on elderly patients presenting with age-related damage to the layers of the aortic wall and with non-perfusion of vital organ systems such as the brain and abdominal organs, since these can be used with a shortened and surgically simpler method.

The three portions of the vascular prosthesis form a unit and can be produced from one piece or are rigidly/fixedly connected to one another, for example by sewing.

Advantageously, the stent portion free of prosthesis material can be released in the expanded state in the area of the aortic arch. This ensures that the blood flow into the branching-off vessels, such as the brachiocephalic trunk, the left common carotid artery and the left subclavian artery, is not impeded. The blood flowing through the aortic arch, and through the vascular prosthesis to be anchored therein, can leave through the openings present in the stent portion of the vascular prosthesis. It is at the same time ensured that the vascular prosthesis is anchored securely in the vessel via the vascular prosthesis portion lying to the left and right of the stent portion. This can be achieved by radial expansion forces of the first vascular prosthesis portion, or of the rings present therein, and by the resulting bearing of the vascular prosthesis on the vessel wall in these areas, and by suturing to the wall of the aorta the second vascular prosthesis portion which, according to the invention, has no meandering rings and supports or only optionally has these.

Therefore, in a further embodiment of the intraluminal vascular prosthesis according to the invention, at least the first vascular prosthesis portion, or rather the rings thereof, and the stent portion free of prosthesis material are made from a self-expanding material or have such a material. Self-expandable materials are known to a person skilled in the art in the field of vascular implants, and an example of a preferred material here is Nitinol.

The prosthesis material used in the vascular prosthesis according to the invention, and provided in the first and second vascular prosthesis portions, is, in an embodiment of the present invention, chosen from polyester, polyurethane, polytetrafluoroethylene or ultra-high-molecular-weight polyethylene (UHMPE) and preferably constitutes a woven polyester fabric.

According to another preferred embodiment, the first vascular prosthesis portion has between two, three, four and five, preferably three, successive rings of meandering supports. These rings are interconnected only by the prosthesis material. The supports or rings themselves are not interconnected by webs or the like and are not in direct contact with one another. This embodiment has the advantage that a person skilled in the art can adapt the length of the vascular prosthesis portion to the particular conditions of the vessel, i.e. in particular to the diameter of the vessel and to the desired length in the vessel.

In the vascular prosthesis according to the invention, provision is made that the first, covered vascular prosthesis portion comes to lie in the distal direction in relation to the subclavian artery, the uncovered stent portion comes to lie in the aortic arch, and the second vascular prosthesis portion comes to lie in the proximal aortic arch.

Here, "proximal" denotes the direction or position closer to the heart, while "distal" denotes the direction or position that lies or comes to lie farther away from the heart.

In other words, the first vascular prosthesis portion is therefore situated at the distal end area of the vascular prosthesis and can therefore also be designated as the distal vascular prosthesis portion, and the second vascular prosthesis portion is situated at the proximal end area of the vascular prosthesis and can therefore be designated as the proximal vascular prosthesis portion. In other words, the uncovered stent portion therefore represents the third vascular prosthesis portion, which represents an uncovered stent portion of the vascular prosthesis.

Generally, the first covered vascular prosthesis portion and the second vascular prosthesis portion, and the uncovered stent portion lying between them, each have a proximal end and a distal end. The distal end of the first vascular prosthesis portion and the proximal end of the second vascular prosthesis portion together form the outermost ends of the vascular prosthesis, wherein the first vascular prosthesis portion is provided at the distal end of the vascular prosthesis, and the second vascular prosthesis portion is provided at the proximal end. The distal end of the second vascular prosthesis portion is connected to the proximal end of the uncovered stent portion, and the distal end of the uncovered stent portion is connected to the proximal end of the first vascular prosthesis portion.

According to a further embodiment, the second vascular prosthesis portion has between zero and five rings of meandering supports arranged in succession. The second vascular prosthesis portion, which comes to lie in the proximal aortic arch, can be sewn on in this area of the aorta, such that this stent graft portion does not necessarily need to have rings/supports.

In another embodiment of the vascular prosthesis according to the invention, the first vascular prosthesis portion has three successive rings of meandering supports, which are connected to one another by the prosthesis material, and the second vascular prosthesis portion is composed only of prosthesis material and has no rings or supports connected indirectly to one another in the prosthesis material.

According to one embodiment, the stent portion free of prosthesis material is a braided or twisted wire braid or has such a wire braid. A "wire braid" is understood here as any configuration of a stent in which different wire strands are intertwined, interlaced or otherwise coupled to form a structure with zones, areas or points at which the strands lie over one another, and with zones or areas that are free of the wire strands and that therefore form openings or windows or meshes.

According to an alternative embodiment, the stent portion free of prosthesis material is a laser-cut tube. This embodiment also has meshes or openings through which the blood carried in the aorta or in the aortic arch can leave the aorta and pass into the branching-off vessels, in particular the brachiocephalic trunk, the left common carotid artery and the left subclavian artery, and thus ensures supply of blood to these vessels.

According to an embodiment, the first and second vascular prosthesis portions have a length of between ca. 20 mm and ca. 100 mm, and the uncovered stent portion has a length of between ca. 30 mm and ca. 100 mm.

The present invention further relates to a method for releasing the intraluminal vascular prosthesis according to the invention, said method having the following steps:

introducing the intraluminal vascular prosthesis in the compressed state into the aorta, in such a way that the whole of the first vascular prosthesis portion is positioned in the distal direction in relation to the subclavian artery;

transferring the intraluminal vascular prosthesis to the expanded state, in such a way that the stent portion free of prosthesis material is released in the aortic arch in the area of the origins of the brachiocephalic trunk, the common carotid artery and the left subclavian artery, and the second vascular prosthesis portion is released in the proximal direction in relation to the origin of the brachiocephalic trunk.

This method ensures that the vascular prosthesis according to the invention is positioned in such a way that the uncovered stent portion allows blood to flow into the branching-off vessels of the brachiocephalic trunk, the common carotid artery and the left subclavian artery.

It will be noted here that the first, covered vascular prosthesis portion ends with its proximal end, namely the end connected to the distal end of the uncovered stent portion, slightly in the distal direction from the origin of the subclavian artery. The uncovered stent portion is now released in the aortic arch, the wire meshes or the openings of the laser-cut stent portion being so wide that there is no danger of blocking the origins of the vessels of the head and neck (brachiocephalic trunk, left common carotid artery, left subclavian artery). In the proximal direction from the origin of the brachiocephalic trunk, the second, stent-free vascular prosthesis portion is released and can be sutured to the proximal aortic arch. This method has the advantage that, if the upper part of the ascending aorta for example has already been replaced, this hemostatic suture will simultaneously encompass the vascular prosthesis.

Thus, the vascular prosthesis according to the invention and the method for introducing and releasing it afford the advantage that a tear or an aneurysm present in the area of the ascending aorta can be treated, as before, by resection and conventional prosthetic management using the second stent graft portion, and, at the same time, any remaining tears of the intima in the proximal descending aorta or in the aortic arch can be safely stabilized, specifically without danger of rupture in the long term. This can also be achieved in particular by the vascular prosthesis being made, for example, 10% to 20% larger and longer than is needed (oversizing).

Particularly in the case of a dissection or complex aneurysm of the thoracic aorta, the surgical outlay and time involved is therefore a third of that needed for operations and systems used hitherto in the prior art, with comparable results, and therefore the risk of the intervention can be significantly lessened.

Further advantages will become clear from the figures and from the following description of preferred illustrative embodiments.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Illustrative embodiments of the invention are shown in the drawing and are explained in more detail in the description below.

DESCRIPTION OF PREFERRED EMBODIMENTS

Figure 1:
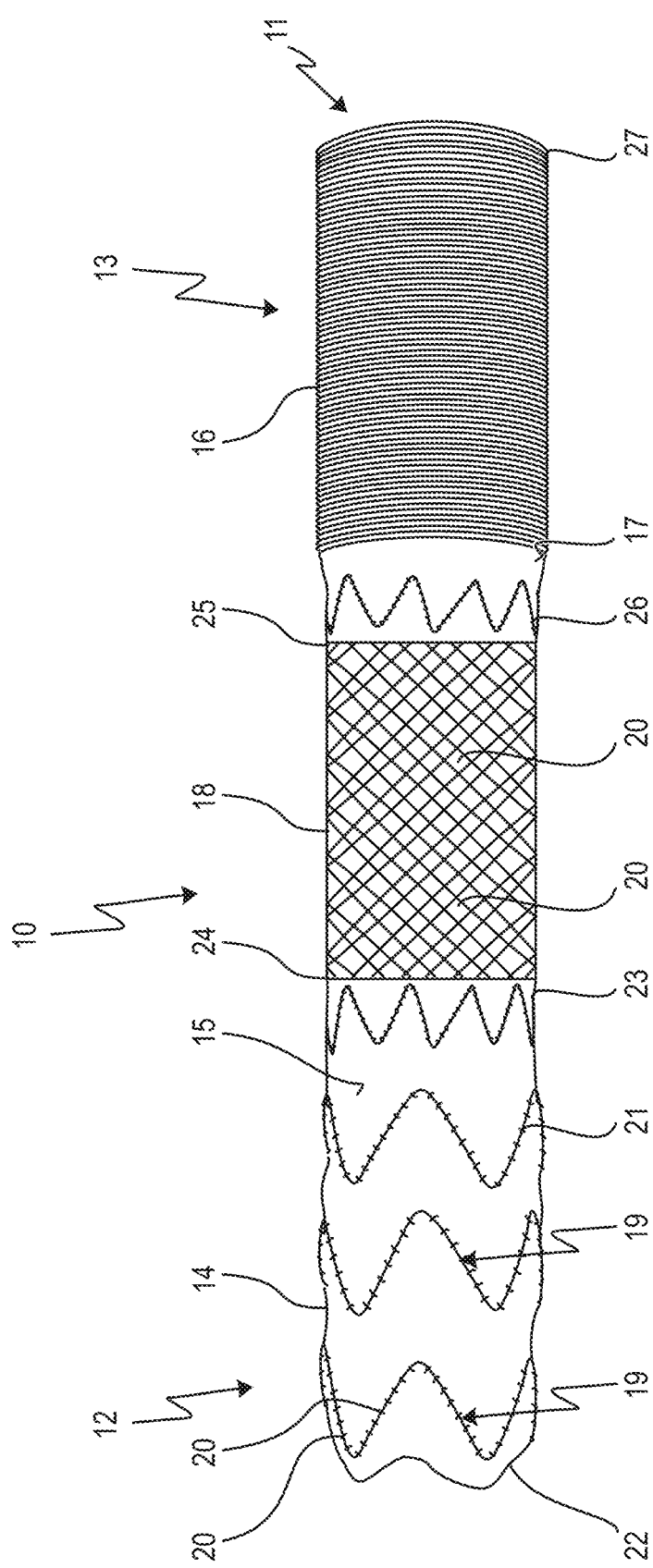
FIG. 1 shows a schematic view of an embodiment of a vascular prosthesis according to the invention (not to scale), in the non-inserted but expanded state.

In FIG. 1, reference number 10 designates the whole of a vascular prosthesis according to the invention, with a hollow cylindrical body 11, and with a first, distal end 12 and a second, proximal end 13. At its distal end 12, it has a first vascular prosthesis portion 14, and, at its proximal end, it has a second vascular prosthesis portion 16. A stent portion 18 is provided centrally between the first vascular prosthesis portion 14 and the second vascular prosthesis portion 16, which stent portion 18 is free of prosthesis material and has open cells or pores 20 through which blood can pass into the branching-off vessels.

The first vascular prosthesis portion 14 and the second vascular prosthesis portion 16 both have a prosthesis material 15, 17, respectively. In the vascular prosthesis shown in FIG. 1, the first vascular prosthesis portion 14 has successive rings 19 of meandering supports 20 which are interconnected only by the prosthesis material 15, to which they are sewn, for example by sutures 21. The meandering supports 20 or rings 19 together form a hollow cylindrical or tubular body. The rings 19 are preferably made of Nitinol. The embodiment of the vascular prosthesis 10 shown in FIG. 1 has four rings 19 in its vascular prosthesis portion 14, although it will be clear to a person skilled in the art that the number of the rings may be different depending on the patient and on the condition and requirements of the vessel.

In the illustrative embodiment shown in FIG. 1, the second vascular prosthesis portion 16 does not have rings or any other stent elements, and instead is composed only of prosthesis material 17, which is shaped in such a way that it likewise forms a hollow cylindrical body. This portion is designated as the cuff. The first vascular prosthesis portion 14 thus constitutes a distal vascular prosthesis portion, the stent portion 18 constitutes the central vascular prosthesis portion, and the second vascular prosthesis portion 16 constitutes the proximal vascular prosthesis portion.

The prosthesis material 15 and 17 is preferably of a material impermeable to blood, preferably woven polyester fabric.

The stent portion 18 of the vascular prosthesis 10 can be a wire braid composed of intertwined Nitinol wires, or it can be a laser-cut Nitinol stent. In both cases, openings or windows or meshes 20 are formed through which blood from the vessel and the vascular prosthesis can pass through and can flow off in surrounding and branching-off vessels.

FIG. 1 also shows in detail the ends of the individual portions 14, 16 and 18 of the vascular prosthesis. Thus, the first vascular prosthesis portion 14 has a distal end 22 and, with its proximal end 23, adjoins the distal end 24 of the stent portion 18, the proximal end 25 of the latter in turn adjoining the distal end 26 of the second vascular prosthesis portion 16 which, with its proximal end 27, forms the outermost proximal end of the vascular prosthesis.

Figure 2:
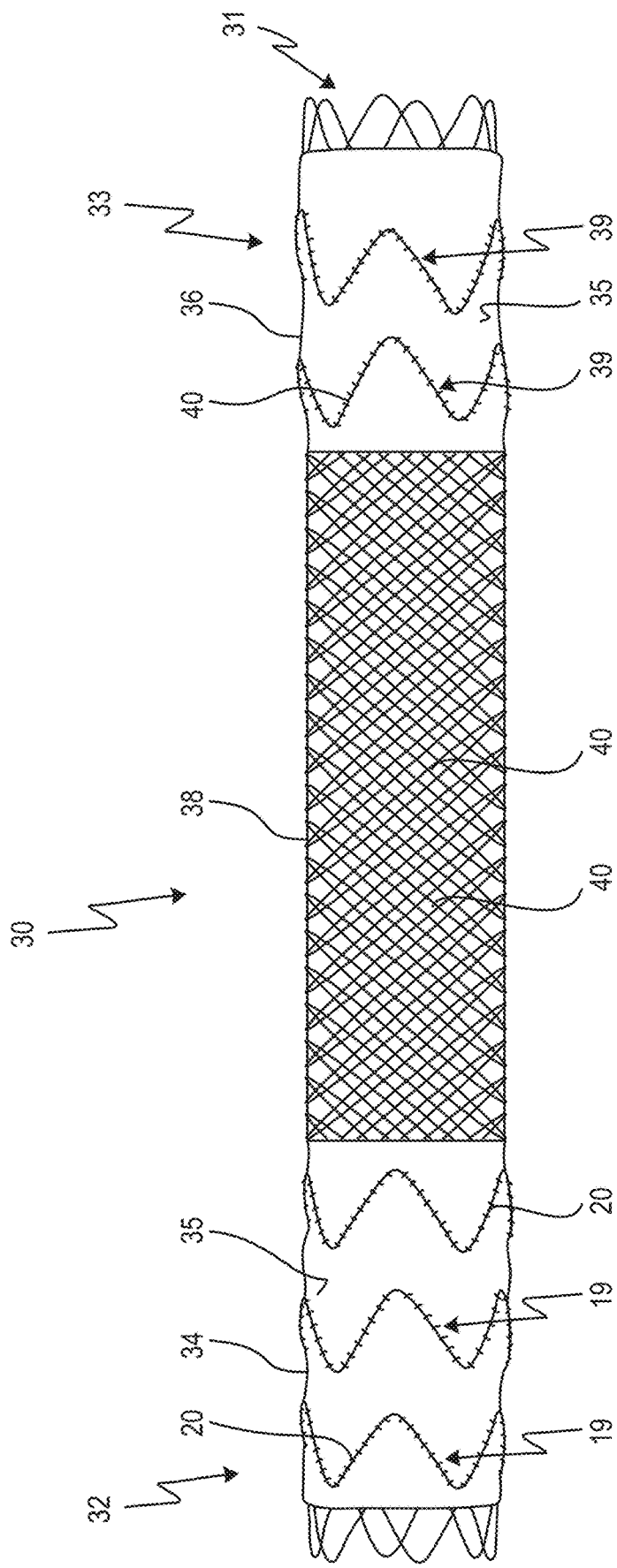
FIG. 2 shows a schematic view of another embodiment of a vascular prosthesis according to the invention (not to scale), likewise in the non-inserted but expanded state.

FIG. 2 shows a further embodiment of a vascular prosthesis 30 according to the invention, where features the same as those of the vascular prosthesis 10 in FIG. 1 are provided with the same reference signs. The vascular prosthesis 30 also has a hollow cylindrical body 31 and a distal end 32 and proximal end 33, and it also has a first vascular prosthesis portion 34 and a second vascular prosthesis portion 36. Like the first stent graft portion 14 of the embodiment 10 shown in FIG. 1, the first vascular prosthesis portion 34 has successive rings 19 of meandering supports 20, which are interconnected by a prosthesis material 35. Moreover, a stent portion that is free of prosthesis material and that has open cells or openings 40 is indicated by 38.

The embodiment 30 shown in FIG. 2 has a second vascular prosthesis portion 36 which, like the first vascular prosthesis portion 34 in this embodiment, has successive rings 19 of meandering supports 20 and is covered by a prosthesis material 35 connecting the rings 19. As in FIG. 1, the first vascular prosthesis portion 34 constitutes a distal vascular prosthesis portion, the stent portion 38 constitutes the central vascular prosthesis portion, and the second vascular prosthesis portion 36 constitutes the proximal vascular prosthesis portion.

Figure 3:
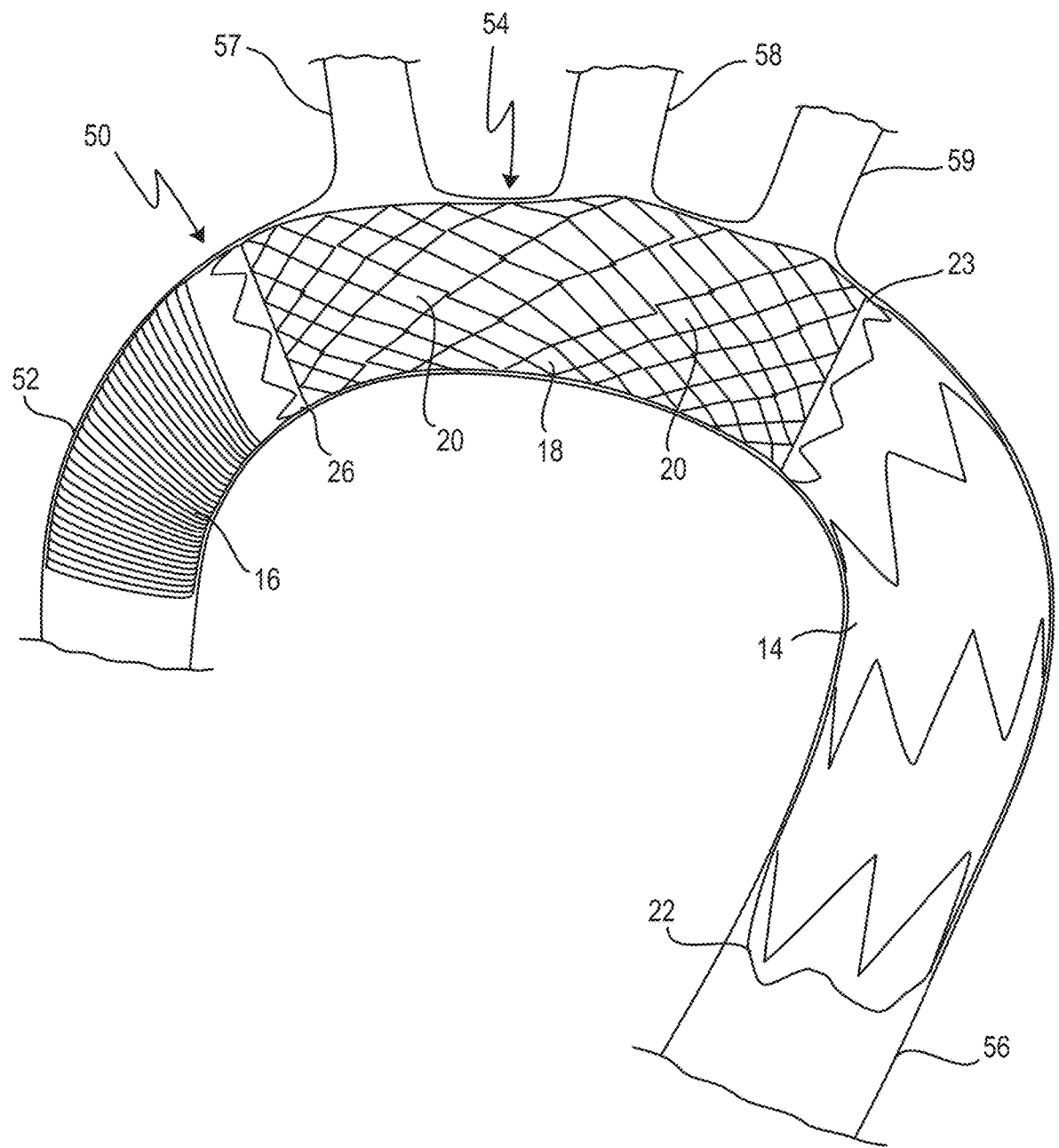
FIG. 3 shows a schematic view of the embodiment from FIG. 1 when positioned and released in the aortic arch.

Finally, in FIG. 3, the embodiment of the vascular prosthesis according to the invention depicted in FIG. 1 is shown in a state when inserted into an aorta 50. In FIG. 3, reference sign 52 designates a part of the ascending aorta, 54 designates the aortic arch, and 56 designates the descending aorta. As will be seen from FIG. 3, three vessels 57, 58 and 59 branch off in the area of the aortic arch 54, namely the brachiocephalic trunk 57, the common carotid artery 58, and the left subclavian artery 59.

FIG. 3 also indicates the placement and positioning of the embodiment of the vascular prosthesis 10 according to the invention shown in FIG. 1. It will be noted that the second vascular prosthesis portion 16, or the distal end 26 thereof, begins in the proximal direction in relation to the brachiocephalic trunk, furthermore that the central stent portion 18 free of prosthesis material is released in the aortic arch 54 and can supply blood to the branching-off vessels 57, 58 and 59 through its cells or openings or meshes 20, and that, finally, the first stent graft portion 14, or the proximal end 23 thereof, begins in the distal direction in relation to the left subclavian artery 59.

For inserting the vascular prosthesis 10, 30 according to the invention, it is loaded onto an insertion system (not shown) and is maintained in a compressed state by a suitable sheath (not shown). Methods and devices for inserting vascular prostheses are known from the prior art and are familiar to a person skilled in the art. The vascular prosthesis 10, 30 maintained in a compressed state is advanced into the descending aorta until the proximal end 23 of the vascular prosthesis 10, 30 lies in the distal direction in relation to the subclavian artery. The correct placement can be monitored, for example, by suitable markers, e.g. radiopaque markers, provided on the vascular prosthesis 10, 30. After correct placement, the vascular prosthesis 10, 30 can now be released by pulling back the sheath, such that, following the first vascular prosthesis portion 14, the uncovered stent portion 18 free of prosthesis material is released in the aortic arch 54, the openings or meshes 20 being so wide that there is no danger of blocking the origins of the vessels 57, 58 and 59 of the head and neck (brachiocephalic trunk, left common carotid aorta, left subclavian artery).

Lastly, in the proximal direction from the origin of the brachiocephalic trunk 57, the second vascular prosthesis portion 16 is now released and can be sutured, for example, to the proximal aortic arch. If the upper part of the ascending aorta 52 has already been replaced, this hemostatic suture will simultaneously encompass this stent graft portion.

It will be clear to a person skilled in the art that he can determine and specifically adapt the exact dimensions and spatial requirements of the individual vascular prosthesis portions, i.e. of the first and second vascular prosthesis portions 14, 16 and of the stent portion 18, by preliminary examination of the patient who is to be treated.

The invention claimed is:

1. An intraluminal vascular prosthesis designed for implantation in the area of the ascending aorta, the aortic arch and the descending aorta in a patient in need thereof, wherein the vascular prosthesis for introduction into the aorta can be transferred from a compressed state to an expanded state, the vascular prosthesis having a hollow cylindrical body with a first end and a second end,
   wherein the vascular prosthesis comprises, at its first end, a first vascular prosthesis portion, with successive rings of meandering supports, and a first prosthesis material secured onto the rings and connecting them,
wherein the vascular prosthesis has, at its second end, a second vascular prosthesis portion consisting exclusively of a second prosthesis material and not having successive rings of meandering supports connected to the second prosthesis material,
   wherein the vascular prosthesis moreover has a tubular stent portion which is provided between the first vascular prosthesis portion and the second vascular prosthesis portion and which is fixedly connected to said vascular prosthesis portions, said tubular stent portion being substantially free of any prosthesis material and consisting of a self-expanding stent material and having meshes or openings, wherein the second prosthesis material of the second vascular prosthesis portion overlaps with the tubular stent portion, such that the tubular stent portion is only covered in the connecting area with the second vascular prosthesis portion and otherwise remains free from prosthesis material,
   and wherein the stent portion is designed for a release in the area of the aortic arc in the area of the origins of the brachiocephalic trunk, the common carotid artery and the left subclavian artery, such, that the stent portion allows blood to flow into the branching-off vessels of the brachiocephalic trunk, the common carotid artery and the left subclavian artery, and wherein the first vascular prosthesis portion for a release in the distal direction in relation to the subclavian artery, and the second vascular prosthesis portion for a release in the proximal direction in relation to the origin of the brachiocephalic trunk.

2. The intraluminal vascular prosthesis as claimed in claim 1, wherein the first vascular prosthesis portion and the second vascular prosthesis portion are designed for anchoring the vascular prosthesis in the aorta.

3. The intraluminal vascular prosthesis as claimed in claim 1, wherein the first vascular prosthesis portion has a self-expanding material.

4. The intraluminal vascular prosthesis as claimed in claim 1, wherein the first vascular prosthesis portion has between two and five rings of successive meandering supports.

5. The intraluminal vascular prosthesis as claimed in claim 1, wherein the first vascular prosthesis portion has three successive rings of meandering supports, which are connected to one another by the prosthesis material.

6. The intraluminal vascular prosthesis as claimed in claim 1, wherein the stent portion free of prosthesis material has a braided or twisted wire braid.

7. The intraluminal vascular prosthesis as claimed in claim 1, wherein the stent portion free of prosthesis material is a laser-cut tube.

8. A method for releasing the intraluminal vascular prosthesis as claimed in claim 1, wherein the method has the following consecutive steps:

introducing the intraluminal vascular prosthesis in the compressed state into an aorta of a patient, in such a way that the whole of the first vascular prosthesis portion is positioned in the distal direction in relation to the subclavian artery;

transferring the intraluminal vascular prosthesis to the expanded state, in such a way that the stent portion free of prosthesis material is released in the aortic arch in the area of the origins of the brachiocephalic trunk, the common carotid artery and the left subclavian artery, and the second vascular prosthesis portion is released in the proximal direction in relation to the origin of the brachiocephalic trunk.

9. The intraluminal vascular prosthesis as claimed in claim 1 for use in the treatment of dissections or aneurysms of the thoracic aorta.

* * * * *